(12) United States Patent
McCook et al.

(10) Patent No.: US 6,706,257 B1
(45) Date of Patent: Mar. 16, 2004

(54) SUNLESS TANNING PRODUCTS AND PROCESSES

(75) Inventors: John P. McCook, Frisco, TX (US); Philip J. Gordon, Plano, TX (US); D. Craig Woodward, Plano, TX (US)

(73) Assignee: Discovery Partners, LLC, Frisco, TX (US)

( * ) Notice: Subject to any disclaimer, the term of this patent is extended or adjusted under 35 U.S.C. 154(b) by 139 days.

(21) Appl. No.: 10/024,822

(22) Filed: Dec. 18, 2001

(51) Int. Cl.[7] ............... A61K 7/42; A61K 7/44; A61K 7/00
(52) U.S. Cl. ............... 424/59; 424/60; 424/400; 424/401
(58) Field of Search .............. 424/59, 60, 400, 424/401

(56) References Cited

U.S. PATENT DOCUMENTS 4,568,547 A * 2/1986 Herschler ............... 514/772
6,399,093 B1 * 6/2002 Petrus et al. ............. 424/448

* cited by examiner

Primary Examiner—Shelley A. Dodson

(57) ABSTRACT

Sunless tanning compositions are substantially improved by adding methylsulfonyl methane [MSM] sequentially or simultaneously to compositions containing dihydroxyacetone [DHA].

5 Claims, No Drawings

SUNLESS TANNING PRODUCTS AND PROCESSES

BACKGROUND OF THE INVENTION

Sunless tanning, also called self-tanning, is the ability to impart a tan to fair or light skin without the use of sunlight. In order to achieve a tanned look or otherwise darken their skin, individuals can expose their skin to sunlight or a source of simulated sunlight, e.g., a solar simulator or ultraviolet lamps. For many individuals, such exposure will stimulate formation of new melanin pigment and retention or increased amount of melanin in the epidermis and produce a darkened skin color. However, some individuals find that such exposure does not produce the desired melanin formation and as a result the desired tan is not obtained. Additionally, exposure to the sun or a source of ultraviolet radiation can have deleterious effects for many individuals and can, in fact, cause sunburn, skin blistering, premature skin aging or skin cancer. Self-tanning or sunless tanning compositions offer a safe alternative and enable these individuals to obtain the desired tanned look.

Commercial formulations, using dihydroxyacetone [DHA], applied locally to the skin, were developed for this purpose. Subsequent formulations using amino acids or amino functional materials when applied sequentially or simultaneously with incorporated DHA produced a faster, more natural and longer lasting artificial effect.

SUMMARY OF THE INVENTION

In experimenting with various compositions for improving sunless tanning formulations, applicant accidentally added methylsulfonyl methane, also known as methyl sulfone, [MSM], instead of the addition of amino acids, and found much to his surprise that the product was a substantially improved formulation.

MSM is claimed to have nutritional properties when taken orally. It is currently popular as a nutritional supplement; When applied topically it can assist in softening skin and nails. However applicant has not found any references suggesting the use of MSM in self-tanning or sun care compositions or suggesting that MSM could enhance penetration of the skin by any topical application thereto.

Applicant used his MSM formulation as a pre-tan accelerator and then applied a conventional self tanner composition not containing MSM. Applicant then used a conventional accelerator and applied the same conventional self tanner composition. Use of applicant's accelerator in this manner produced a darker and more intense tan then use of accelerators containing amino acids but without MSM. More particularly, skin sites treated with MSM or MSM plus amino acids in the pre-tan accelerator plus the self tanner had a longer lasting and darker tan than the skin sites treated with no MSM or with an amino acid containing pre-tan accelerator and a self tanner.

Applicant also incorporated MSM in self tanner formulations containing DHA and used it in comparison with formulations that contained no MSM. The tan produced by applicant's formulation remained darker and lasted several days longer then the conventional self-tanning formulation.

Applicant has conducted experiments with a typical oil-in-water self tanning cream containing DHA as the self tanning agent with or without the inclusion of MSM. The self tanning composition using MSM produced a tan that developed at a more rapid rate, was more intense, and lasted longer than the same composition without MSM. Applicant also conducted experiments with DHA containing self-tanning liquid mousse compositions, with and without MSM. Again, the self-tanning composition with MSM produced a tan that developed at a more rapid rate, was more intense, and lasted longer than the same composition without MSM.

Consequently, in accordance with the principles of this invention, MSM enhances the performance of DHA containing self-tanning compositions when used sequentially, simultaneously, or subsequently in conjunction with self-tanners. MSM does not react chemically with DHA but it acts as if it is a skin penetrant to facilitate DHA penetration.

Additions of 5% MSM to DHA formulas, either with or without soluble dyes, enhances tanning effect producing a more intense hue that lasts longer. The use of MSM as an accelerator also produces a more intense hue. The best results were produced with an addition of 5% MSM. Similar but less pronounced effects were obtained with additions as low as 1% and as high as 20%. A 0.1% addition of MSM was ineffective. The solubility of MSM in water is limited to about a 20% addition so additions above this range were not attempted.

The following examples will more fully illustrate the embodiments of this invention. All parts, percentages and proportions referred to herein and in the appended claims are by weight unless otherwise indicated.

Example 1 is a known liquid or liquid/foaming mousse sunless tanning formula that does not contain MSM. Example 2 is an otherwise identical formula but also contains 5% MSM. In both formulas citric acid 25% solution was use to adjust pH to 3.25–3.75. Both formulas contain DHA that produces a tan several hours after application and a soluble dye system than produces an immediate darkening to facilitate an even application. The soluble dye system rinses off with showering or bathing leaving a tanned skin from the DHA reaction.

EXAMPLE 1

Sunless Tanning Formula [Liquid Mousse]

| PHASE | INGREDIENTS | PERCENT |
|---|---|---|
| A | Water | qs to 100% |
|   | Hydroxyethylcellulose |  |
| B | Methyl Gluceth-20 | 1.00 |
|   | Glycereth 26 | 1.25 |
| C | Dihydroxyacetone | 5.00 |
| D | Decyl Glucoside | 1.5 |
| E | Phenonip | 1.00 |
| F | FD%C Red #4 solution | qs to standard |
|   | FD%C Blue #1 solution | qs to standard |
|   | FD%C Yellow #6 solution | qs to standard |
|   | FD%C Yellow #5 solution | qs to standard |

EXAMPLE 2

Identical with Example 1 except 5% MSM has been added.

Both formulas in Examples 1 and 2 were applied to the inside portion of the arm in two adjacent sites to untanned Caucasian skin of approximately the same color. Petrolatum was applied between the two test sites to prevent crossover migration. Approximately 200 mg of each formulation was applied with a cotton swab to produce a uniform application of the test formula in a 2.5 inch by 2.5 inch test area. The test sites were washed about 12 hours later and initial readings were taken with Minolta CR-10 Colorimeter. During the testing period, the test sites were protected from sunlight by avoiding sun exposure or by covering the sites with clothing. The hue intensity was measured. The intensity is equal to the square root of value a squared plus value b squared, both values being the readings of the Colorimeter.

The comparative hue intensity of formula 2 as compared to formula 1 for day 1, day 2, day 7 and day 9 were +0.2, +0.3, +0.3 and 0.0, thus demonstrating the advantages of using MSM.

EXAMPLE 3

Pre Tan Accelerator Containing 0.1% MSM

| PHASE | INGREDIENTS | PERCENT |
|---|---|---|
| A | Water | 86.50 |
|  | Hispagel Oil HV | 5.00 |
|  | Methyl Gluceth-20 | 1.00 |
|  | Glycereth 26 | 2.00 |
|  | Ethoxydiglycol | 2.00 |
|  | MFA Complex | 2.00 |
|  | TEA 99% [Triethanolamine] | 1.00 |
| B | Germaben II | 1.0 |
| C | MSM | 0.10 |
|  |  | 100.00 |

EXAMPLES 4, 5 and 6

These examples are identical with example 3 except that example 4 contains 1% MSM; example 5 contains 5% MSM and example 6 contains 20% MSM. As compared to the same formulation without MSM, the hue intensities over the same time periods as employed on Examples 1 and 2 for 1% MSM were −0.7, +0.1, +0.8 and 0.0 respectively. For 5% MSM, the intensities were +2.1, +3.9, +2.7 and +2.1. For 20% MSM, the intensities were −0.1, +0.3, +1.5 and 0.0.

EXAMPLE 7

Self Tanning Cream With 5.00% MSM

| PHASE | INGREDIENTS | PERCENT |
|---|---|---|
| A | Water | 46.00 |
|  | Carbopol 940 [2% dispersion in water] | 10.00 |
|  | Disodium EDTA | 0.10 |
|  | Glycerin | 1.00 |
| B | Cetyl Alcohol | 4.00 |
|  | Lipomulse 165 | 4.00 |
|  | Finsolv TN | 4.00 |
|  | Dimethicone | 0.50 |
| C | Water | 8.00 |
|  | Dihydroxyacetone | 5.00 |
| D | Water | 10.00 |
|  | MSM | 5.00 |
| E | Water | 1.00 |
|  | Triethanolamine 99% | 0.40 |
| F | Phenonip | 1.00 |
|  |  | 100.00 |

Citric Acid 25% solution used to adjust pH to 5.03

EXAMPLE 8

Self Tanning Cream Without MSM

| PHASE | INGREDIENTS | PERCENT |
|---|---|---|
| A | Water | 61.00 |
|  | Carbopol 940 [2% dispersion in water] | 10.00 |
|  | Disodium EDTA | 0.1 |
|  | Glycerin | 1.00 |
| B | Cetyl Alcohol | 4.00 |
|  | Lipomulse 185 | 4.00 |
|  | Finsolv TN | 4.00 |
|  | Dimethicone | 0.50 |
| C | Water | 8.00 |
|  | Dihydroxyacetone | 5.00 |
| D | Water | 10.00 |
|  | Dihydroxyacetone | 5.00 |
| E | Phenonip | 1.00 |
|  |  | 100.00 |

Citric Acid 25% solution used to adjust pH to 4.98.

Formulas 7 and 8 were compared in the same manner as above. Formula 7 with 5% MSM as compared to Formula 8 with no MSM displayed the same type of comparison hue intensities for day 2 of +2.0, day 7 of +0.4 and day 9 as +0.2.

While in the above examples, water was used as a solvent, as is known in the art, water is at least one of the solvents that can be used, as it is shelf stable, safe for human skin application, dries relatively quickly and is non-greasy. Other solvents such as ethanol and volatile silicones can be used, alone or in combination with water or each other.

While in the above examples, the formulations were in liquid or cream but could also be used in gel or foam arrangements.

While the examples set forth above illustrate specific embodiments of the invention and should be considered non-limiting examples with variations and modifications thereof all being within the spirit and purview of this invention.

What is claimed is:

1. A self-tanning formulation comprising:
   1%–20% MSM;
   0.5%–20% DHA;
   at least one solvent that is shelf stable, safe for human skin application, dries relatively quickly and is non-greasy, said solvent being selected from at least one member of the group consisting of water, ethanol, volatile silicones;
   said MSM and solvent being in the form of a liquid, foam, lotion, cream or gel.

2. The formulation of claim 1 containing 5% MSM.

3. The formulation of claim 2 wherein the pH is maintained in the range of 3.0–6.0.

4. An accelerator for sunless tanning formulations comprising:
   1%–20% MSM;
   at least one solvent that is shelf stable, safe for human skin application, dries relatively quickly and is non-greasy, said solvent being selected from at least one member of the group consisting of water, ethanol, volatile silicones;
   said MSM and solvent being in the form of a liquid, foam, lotion, cream or gel.

5. The accelerator of claim 4 containing 5% MSM.

* * * * *